(12) United States Patent
Gray-Dreizler et al.

(10) Patent No.: US 9,533,061 B2
(45) Date of Patent: Jan. 3, 2017

(54) SURGICAL STERILIZING CONTAINER TUB AND SURGICAL STERILIZING CONTAINER WITH A STERILIZING CONTAINER TUB

(71) Applicant: Aesculap AG, Tuttlingen (DE)

(72) Inventors: John Gray-Dreizler, Rottweil (DE); Wilhelm Gleichauf, Tuttlingen-Moehringen (DE); Mariana Jakab, Tuttlingen (DE); Stefan Thomas, Tuttlingen (DE); Stefan Schuster, Villingen-Schwenningen (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 14/452,896

(22) Filed: Aug. 6, 2014

(65) Prior Publication Data

US 2015/0004075 A1 Jan. 1, 2015

Related U.S. Application Data

(63) Continuation of application No. PCT/EP2013/053533, filed on Feb. 22, 2013.

(30) Foreign Application Priority Data

Mar. 5, 2012 (DE) .......................... 10 2012 101 833

(51) Int. Cl.
*A61L 2/26* (2006.01)
*A61B 50/30* (2016.01)
(Continued)

(52) U.S. Cl.
CPC .................. *A61L 2/18* (2013.01); *A61B 50/30* (2016.02); *A61L 2/26* (2013.01); *A61B 2050/006* (2016.02);
(Continued)

(58) Field of Classification Search
CPC ...................................... A61L 2/18; A61L 2/07
(Continued)

(56) References Cited

U.S. PATENT DOCUMENTS 2,673,379 A 3/1954 Jewell et al.
3,437,423 A 4/1969 Mondiadis
(Continued)

FOREIGN PATENT DOCUMENTS

DE 37 11 621 10/1987
DE 3929906 12/1990
(Continued)

*Primary Examiner* — Kevin Joyner
*Assistant Examiner* — Holly Mull
(74) *Attorney, Agent, or Firm* — Lipsitz & McAllister, LLC

(57) ABSTRACT

A surgical sterilizing container tub is provided on which a sterilizing container lid is adapted to be detachably fitted for formation of a surgical sterilizing container for holding surgical instruments for sterilization. The sterilizing container tub has a bottom and a container wall projecting from the bottom. The sterilizing container tub defines a set-down plane, and the bottom forms a fluid collection area for collecting fluid. In order to provide such a surgical sterilizing container tub and such a surgical sterilizing container with which fluid to be removed can be effectively conducted to the fluid collection area, the bottom has a fluid drainage surface which is inclined relative to the set-down plane and is in fluid connection with the fluid collection area for draining fluid in the direction of the container wall. A surgical sterilizing container is also provided.

15 Claims, 7 Drawing Sheets

(51) Int. Cl.
*A61L 2/18* (2006.01)
*A61L 2/07* (2006.01)

(52) U.S. Cl.
CPC .......... *A61B 2050/0074* (2016.02); *A61L 2/07* (2013.01); *A61L 2202/182* (2013.01)

(58) Field of Classification Search
USPC ........................................................ 422/292
See application file for complete search history.

(56) References Cited

U.S. PATENT DOCUMENTS

| | | | |
|---|---|---|---|
| 4,247,517 A | | 1/1981 | Sanderson et al. |
| 4,251,482 A | | 2/1981 | Sanderson et al. |
| 4,416,417 A | | 11/1983 | Sanderson et al. |
| 4,671,943 A | * | 6/1987 | Wahlquist ................ A61L 2/26 206/363 |
| 4,900,519 A | | 2/1990 | Nichols |
| 5,366,693 A | | 11/1994 | Burgos et al. |
| 5,441,707 A | | 8/1995 | Lewis et al. |
| 5,869,000 A | | 2/1999 | DeCato |
| 5,971,152 A | | 10/1999 | Bowsman |
| 6,150,159 A | | 11/2000 | Fry |
| 6,367,651 B2 | | 4/2002 | Laib et al. |
| 6,620,390 B1 | | 9/2003 | Wagner |
| 6,821,286 B1 | | 11/2004 | Carranza et al. |
| 7,641,852 B1 | | 1/2010 | McPhail et al. |
| 2001/0047997 A1 | | 12/2001 | Laib et al. |
| 2002/0090333 A1 | * | 7/2002 | Chang ...................... A61L 2/04 422/300 |
| 2004/0126274 A1 | * | 7/2004 | Song ........................ A61L 2/26 422/26 |
| 2005/0109055 A1 | * | 5/2005 | Goetzinger ........... F24F 13/222 62/291 |
| 2008/0236631 A1 | * | 10/2008 | Lin .......................... A61L 2/07 134/26 |
| 2011/0262301 A1 | | 10/2011 | Ghelman et al. |
| 2013/0175276 A1 | | 7/2013 | Gleichauf et al. |

FOREIGN PATENT DOCUMENTS

| | | |
|---|---|---|
| DE | 198 27 442 | 12/1998 |
| DE | 197 53 671 | 6/1999 |
| DE | 198 30 460 | 11/1999 |
| DE | 600 11 879 | 8/2005 |
| DE | 10 2004 028 040 | 10/2005 |
| EP | 0336047 | 10/1989 |
| EP | 1 016 369 | 7/2000 |
| EP | 1 035 873 | 6/2002 |
| EP | 1 647 285 | 4/2006 |
| FR | 2 542 200 | 9/1984 |
| WO | WO 99/27969 | 6/1999 |
| WO | WO 2008/061137 | 5/2008 |
| WO | WO 2012/038314 | 3/2012 |

* cited by examiner

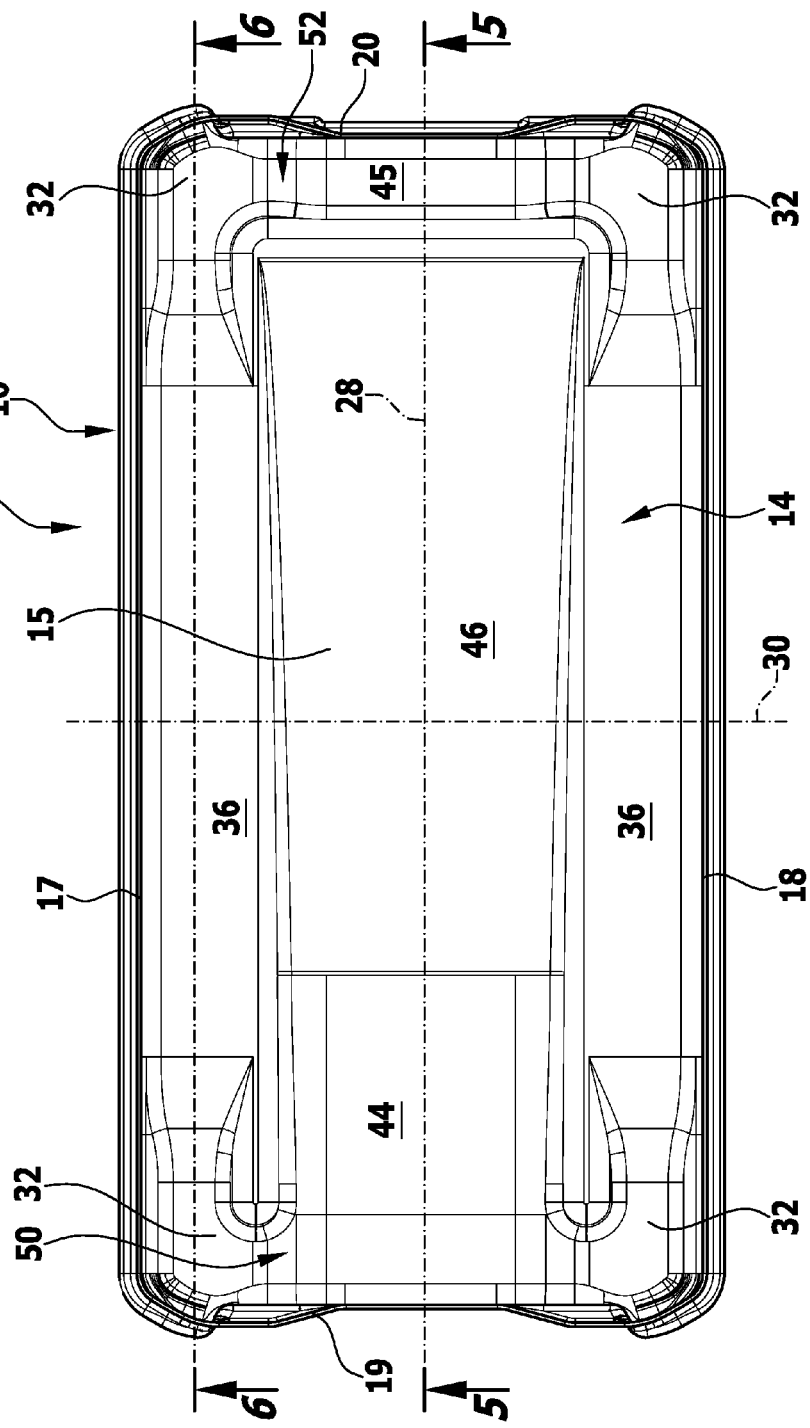

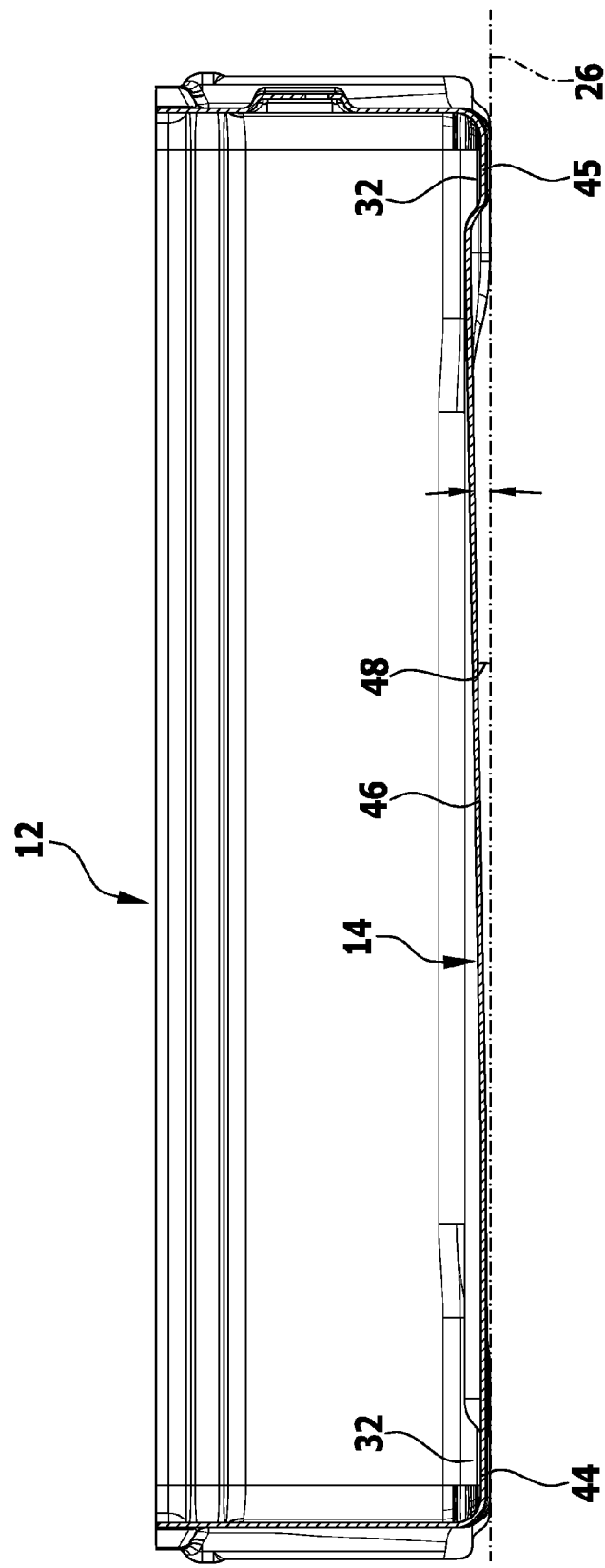

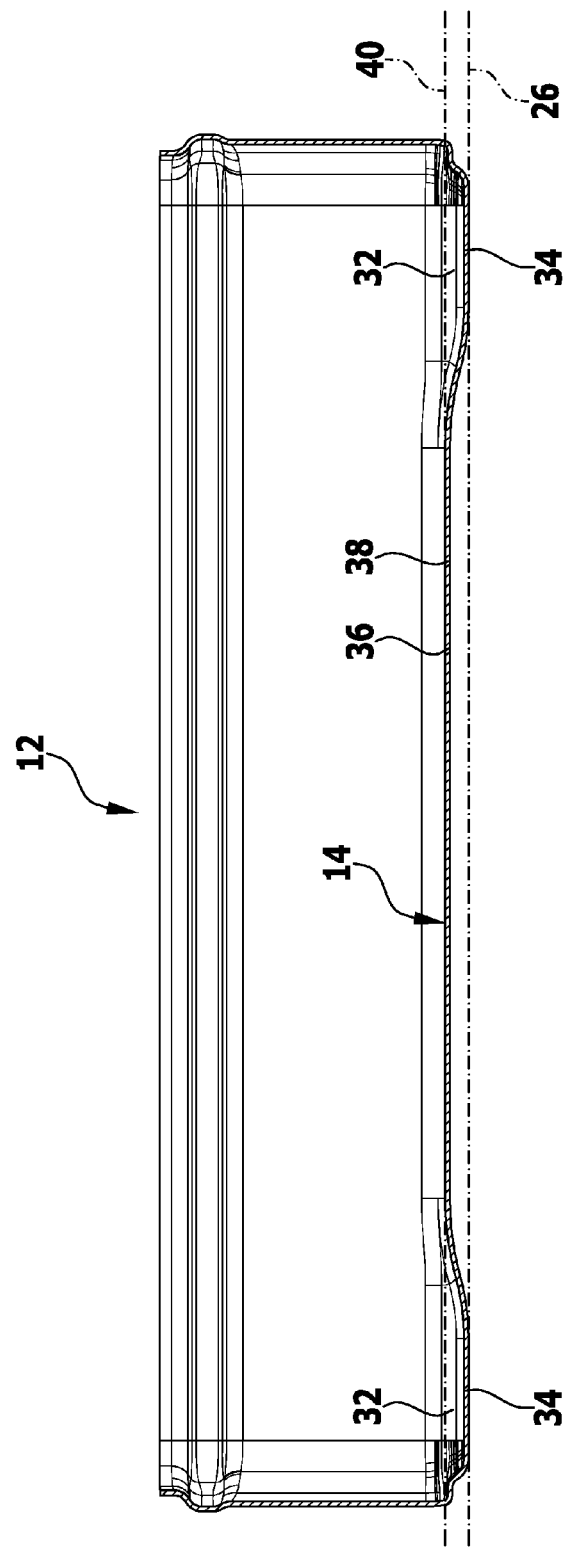

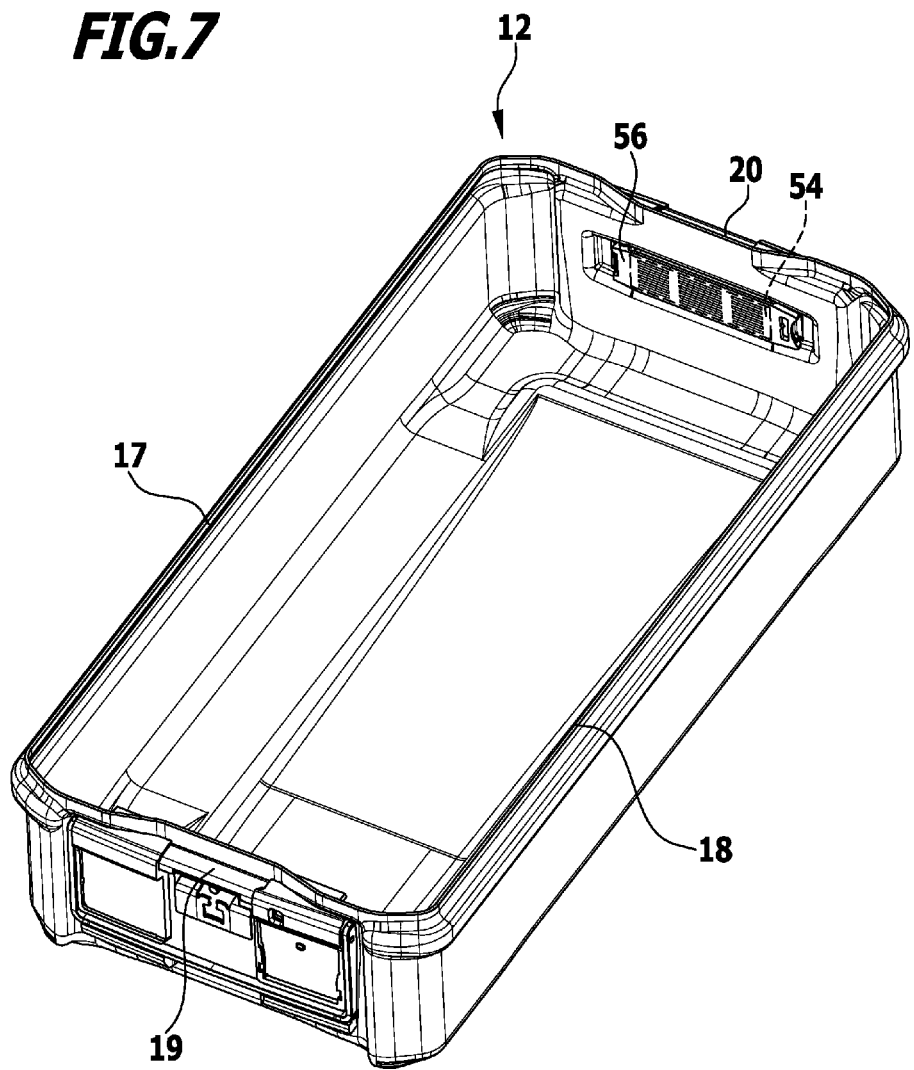

SURGICAL STERILIZING CONTAINER TUB AND SURGICAL STERILIZING CONTAINER WITH A STERILIZING CONTAINER TUB

CROSS-REFERENCE TO RELATED APPLICATIONS

This application is a continuation of international application number PCT/EP2013/053533, filed on Feb. 22, 2013, and claims the benefit of German application number 10 2012 101 833.2, filed on Mar. 5, 2012, which are incorporated herein by reference in their entirety and for all purposes.

FIELD OF THE INVENTION

The present invention relates to a surgical sterilizing container tub on which a sterilizing container lid is adapted to be detachably fitted for formation of a surgical sterilizing container for holding surgical instruments for sterilization, the sterilizing container tub comprising a bottom and a container wall projecting from the bottom, the sterilizing container tub defining a set-down plane, and the bottom comprising or forming a fluid collection area for collecting fluid.

The present invention also relates to a surgical sterilizing container, comprising a surgical sterilizing container tub and a sterilizing container lid adapted to be detachably fitted on the sterilizing container tub.

BACKGROUND OF THE INVENTION

Sterilizing containers with sterilizing container tubs of the kind mentioned at the outset having a trough-shaped fluid collection area arranged at the center of their bottom are known. Formed at the fluid collection area in the bottom is a through-opening at which a pressure-controlled or temperature-controlled outlet valve is arranged, with which the through-opening can be closed and opened. Fluid such as, in particular, condensate forming during the sterilization process can be drained from the sterilizing container through the bottom when the outlet valve is open. However, this has the great inherent disadvantage that drained condensate exits from the sterilizing container in a gush. Where sterilizing containers are stacked one on top of the other, the condensate can flow from the higher sterilizing container over the lid of the sterilizing container below it. This results in undesired cooling of the lower sterilizing container and in undesired subsequent formation of condensate in its container interior. The condensate has to be drained off additionally or evaporated additionally during the drying phase.

Furthermore, the provision of a through-opening in the bottom proves to be disadvantageous. If the outlet valve is faulty or damaged, the sterilizing container is inadequately sealed. This may lead to unsatisfactory sterilization results and facilitate penetration of germs into the container interior. Undesired opening, damage to or failure of the outlet valve may, for example, be caused by unevenesses of a set-down surface or by objects on a set-down surface for the sterilizing container, which act from below on the outlet valve. It also proves disadvantageous that owing to the arrangement of the opening in the bottom it is difficult for hospital staff normally handling the sterilizing container to recognize damage to the outlet valve.

"Set-down surface" is a contact plane which is defined by the sterilizing container tub and in which the sterilizing container tub contacts a set-down surface on which the sterilizing container tub is set down. The horizontally aligned set-down surface, as is usually the case, will, when the sterilizing container tub is used in accordance with the specifications in an operating position, result in a horizontal alignment of the set-down or contact plane.

An object underlying the present invention is to provide a surgical sterilizing container tub and a surgical sterilizing container of the kind mentioned at the outset, with which fluid to be removed can be effectively conducted to the fluid collection area.

SUMMARY OF THE INVENTION

In a first aspect of the invention, a surgical sterilizing container tub on which a sterilizing container lid is adapted to be detachably fitted for formation of a surgical sterilizing container for holding surgical instruments for sterilization is provided. The sterilizing container tub comprises a bottom and a container wall projecting from the bottom, the sterilizing container tub defines a set-down plane, and the bottom comprises or forms a fluid collection area for collecting fluid. The bottom comprises a fluid drainage surface which is inclined relative to the set-down plane and is in fluid connection with the fluid collection area for draining fluid in the direction of the container wall.

In a second aspect of the invention, a surgical sterilizing container is provided, comprising a surgical sterilizing container tub and a sterilizing container lid adapted to be detachably fitted on the sterilizing container tub. The surgical sterilizing container is adapted for holding surgical instruments for sterilization. The sterilizing container tub comprises a bottom and a container wall projecting from the bottom, the sterilizing container tub defines a set-down plane, and the bottom comprises or forms a fluid collection area for collecting fluid. The bottom comprises a fluid drainage surface which is inclined relative to the set-down plane and is in fluid connection with the fluid collection area for draining fluid in the direction of the container wall.

BRIEF DESCRIPTION OF THE DRAWINGS

The foregoing summary and the following description may be better understood in conjunction with the drawing figures. There are shown in:

FIG. 4 a plan view of a sterilizing container tub of the sterilizing container from FIG. 1;

FIG. 5 a sectional view along line 5-5 in FIG. 4;

FIG. 6 a sectional view along line 6-6 in FIG. 4; and

FIG. 7 a perspective representation of a sterilizing container tub of the sterilizing container from FIG. 1.

DETAILED DESCRIPTION OF THE INVENTION

Figure 1:
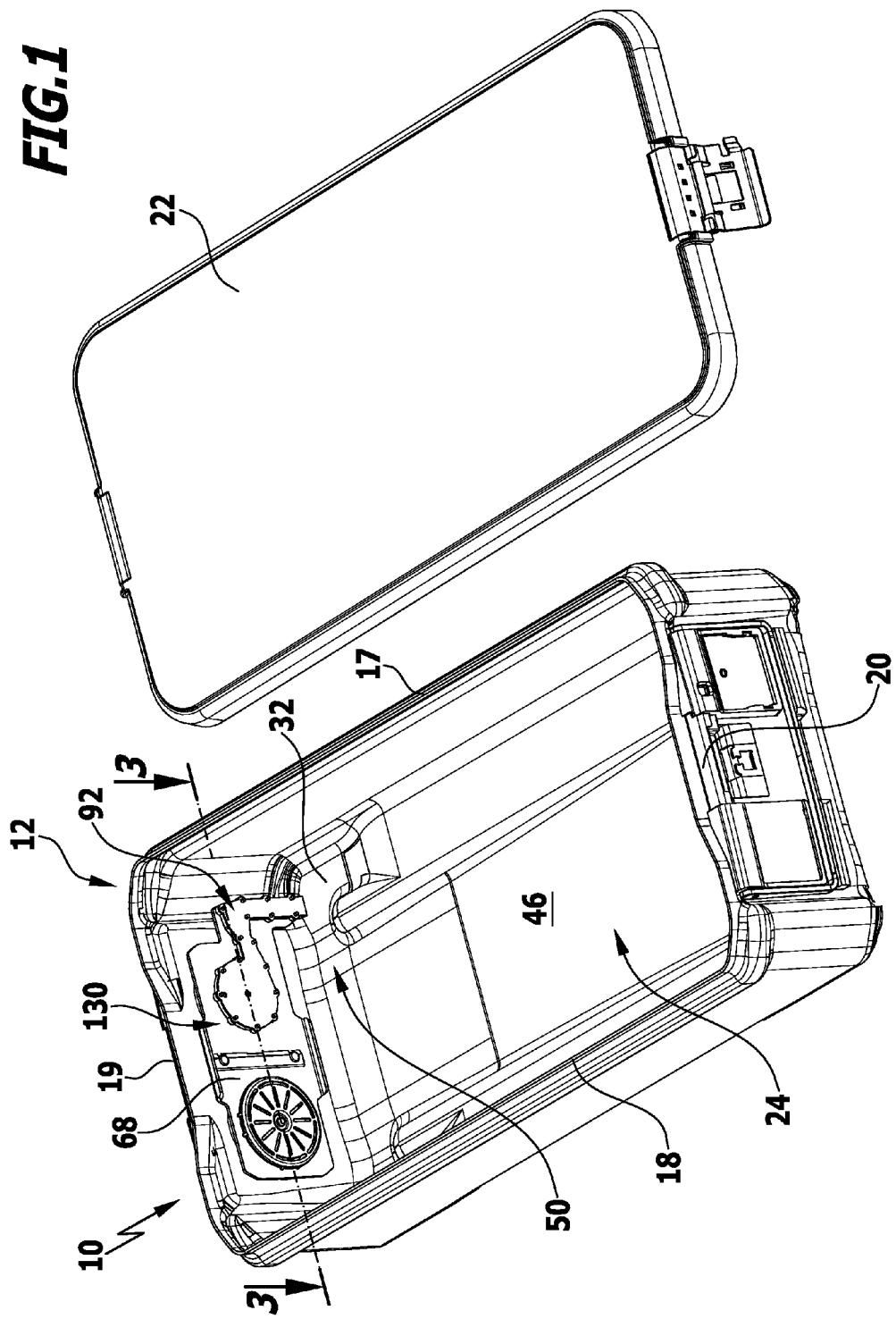
FIG. 1 a perspective representation of a sterilizing container in accordance with the invention in the open state, comprising a sterilizing container tub in accordance with the invention and a fluid extraction device.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a surgical sterilizing container tub on which a sterilizing container lid is adapted to be detachably fitted for formation of a surgical sterilizing container for holding surgical instruments for sterilization, the sterilizing container tub comprising a bottom and a container wall projecting from the bottom, the sterilizing container tub defining a set-down plane, and the bottom comprising or forming a fluid collection area for collecting fluid. The bottom comprises a fluid drainage surface which is inclined relative to the set-down plane and is in fluid connection with the fluid collection area for draining fluid in the direction of the container wall.

A drainage surface which is inclined relative to the set-down plane is provided in the sterilizing container tub in accordance with the invention. In particular, this is to be understood as meaning that the drainage surface does not lie in the set-down plane or is not aligned parallel thereto. The drainage surface allows fluid to be conducted into the fluid collection area, more particularly, in the direction of the container wall of the sterilizing container tub. This makes it possible to conduct fluid such as, in particular, condensate formed during the sterilization process specifically away from the center of the bottom in the direction of the container wall and into the fluid collection area. In this way, the distance of the fluid drained off with the drainage surface from the container wall is reduced. This makes it possible, for example, to use residual heat of the container wall during the drying phase following the sterilization process more effectively than in a conventional sterilizing container tub as the evaporation of fluid is facilitated by the proximity to the container wall. Draining fluid by way of the fluid drainage surface in the direction of the container wall and collecting it in the fluid collection area also allow the fluid to be removed from the sterilizing container tub in a different way than with the sterilizing containers described hereinabove. To do so, a through-opening can, for example, be provided, which is formed in the container wall and at which an outlet valve is arranged for opening and closing the through-opening. Fluid drained off in the direction of the container wall can, in this case, exit from the sterilizing container tub at the side through the container wall when the outlet valve is open. The disadvantages of the sterilizing container described hereinabove, in which fluid is drained off downwards, are, in this way, avoidable to a large extent.

Especially in the last-explained embodiment of the sterilizing container tub, in which a through-opening is formed in the container wall, it is expedient for the bottom to be free of through-openings at the fluid collection area. This allows a sterile barrier to be formed by the bottom at the fluid collection area and leakage from the sterilizing container tub to be avoided.

The bottom is preferably free of through-openings, also outside of the fluid collection area. The entire bottom can thereby form a sterile barrier, and leakage from the sterilizing container tub is avoided.

In an implementation of an advantageous sterilizing container tub, it proves expedient for the size of the fluid drainage surface to be at least 10% of the bottom surface, preferably at least 20% of the bottom surface, even more preferred at least 30% of the bottom surface.

For example, in a preferred embodiment of the sterilizing container tub it proves expedient for the size of the fluid drainage surface to be approximately one third of the bottom surface.

In a different advantageous embodiment, it has proven expedient for the size of the fluid drainage surface to be from approximately 40% to approximately 50% of the bottom surface.

In an implementation of the sterilizing container tub in practice, it proves expedient for the inclination of the fluid drainage surface relative to the set-down plane to be less than 10°, in order to expediently obtain a low constructional height of the bottom. An inclination of the fluid drainage surface relative to the set-down plane of less than 5° has proven to be preferred, even more preferred less than 2°.

In an advantageous embodiment of the sterilizing container tub in accordance with the invention, it has proven expedient for the inclination of the fluid drainage surface relative to the set-down plane to be approximately 1.5°.

The fluid collection area is preferably formed by a depression in the bottom. This makes a constructionally simple configuration of the sterilizing container tub possible.

It is advantageous for the sterilizing container tub to comprise a bottom wall forming the bottom and for the bottom wall to form the fluid drainage surface and/or the fluid collection area. This allows a constructionally simple configuration of the sterilizing container tub to be achieved. In particular, a bottom insert positionable on a bottom wall of the sterilizing container tub can thereby be dispensed with.

The bottom wall is, preferably at least at the fluid collection area, and, in an expedient manner entirely, free of openings, in order to form a sterile barrier and avoid leakage from the sterilizing container tub.

It is advantageous for the fluid collection area to be arranged off-center on the bottom. In particular, this can be taken to mean that the fluid collection area is at a distance from a center of the bottom. This allows fluid drained off by means of the fluid drainage surface to be drained off as close as possible to the container wall.

The fluid collection area is preferably in direct fluid connection with the container wall. This makes it possible to drain fluid off directly to the container wall. For example, a section of the container wall forms a wall of the fluid collection area.

It proves advantageous for the fluid collection area to extend along a section of the container wall, for example, for formation of the aforementioned preferred embodiment. In particular, this is understood as meaning that the fluid collection area is arranged along a section of the container wall and/or that the fluid collection area is adjacent to a section of the container wall. In particular, this can be understood as meaning that the fluid collection area is in direct fluid connection with a section of the container wall.

It is expedient for the sterilizing container tub to be of rectangular or substantially rectangular cross section with four side walls forming the container wall, and for the fluid drainage surface to be inclined in the direction of one of the side walls for draining fluid in the direction of the side wall. "Inclined in the direction of one of the side walls" can, in particular, be understood as meaning that the distance of the fluid drainage surface from the set-down plane at a section of the fluid drainage surface that faces the side wall is less than at a section of the fluid drainage surface that faces away from the side wall. In this embodiment, it is possible to drain fluid off in the direction of one of the side walls. In particular, it may be provided that there is formed in this side wall a through-opening which is closable by an outlet valve and through which fluid collected in the fluid collection area can exit from the sterilizing container tub.

The fluid collection area is preferably adjacent to that side wall in the direction of which the fluid drainage surface is inclined for draining off fluid. It can thereby be ensured that fluid can be conducted from the drainage surface as close as possible to the side wall. In this case, "adjacent" can, in particular, be understood as meaning that the fluid collection area extends along the side wall, and, in particular, is in direct fluid connection with the container wall.

It is advantageously provided that the fluid drainage surface is inclined in the direction of only one of the side walls of the container wall, so that as far as possible fluid is drained off substantially only in the direction of one of the side walls.

It proves advantageous for the container wall to comprise two longitudinal side walls and two transverse side walls and for the fluid drainage surface to be inclined in the direction of one transverse side wall for draining off fluid in the direction of the transverse side wall. In this embodiment, it is possible to drain fluid off in the direction of a transverse side and, therefore, a narrow side of the sterilizing container tub. This makes a more compact configuration of the fluid collection area possible, in particular, when it is arranged along or adjacent to the transverse side wall. A through-opening which is closable by an outlet valve and through which fluid can exit from the sterilizing container tub can be formed in the transverse side wall.

The fluid drainage surface preferably extends beyond the center of the bottom so that fluid can also be drained off from the center of the bottom in the direction of the container wall. For example, in a rectangular sterilizing container tub it may be provided that the fluid drainage surface extends along a longitudinal direction over approximately 60% to approximately 70% of the bottom and in a transverse direction over approximately 45% to approximately 55% of the bottom surface, with the fluid drainage surface extending beyond its center.

For a constructionally simple configuration, it proves expedient for the fluid drainage surface to be of planar configuration. In addition, fluid can be reliably drained off into the fluid collection area via the planar fluid drainage surface.

As mentioned above, it is provided in a preferred embodiment of the sterilizing container tub in accordance with the invention that a through-opening is formed in the container wall, and that the sterilizing container tub comprises an outlet valve or such an outlet valve with which the through-opening is openable and closable is fixed to the sterilizing container tub. Fluid conducted to the fluid collection area can exit from the sterilizing container tub through the through-opening. For this purpose, the fluid collection area is preferably adjacent to a section of the container wall comprising the through-opening or extends along this section.

It proves advantageous for the sterilizing container tub to comprise a fluid lifting device or for such a fluid lifting device to be fixed to the sterilizing container tub for providing a fluid connection from the fluid collection area to the outlet valve and for lifting fluid from the fluid collection area to the outlet valve, the outlet valve being expediently arranged at a distance from the bottom on the container wall. The fluid lifting device makes it possible to lift collected fluid to the outlet valve so that it can exit from the sterilizing container tub. For example, the fluid lifting device comprises a fluid channel which engages the fluid collection area with a fluid inlet opening. The fluid channel may comprise a fluid outlet opening which, for example, is arranged at an upward flow side of the outlet valve or is directed at it. When the outlet valve opens, a flow can form through the through-opening, under the action of which fluid is lifted through the fluid channel to the outlet valve and can exit from the sterilizing container tub.

As mentioned above, the fluid drainage surface is preferably inclined in the direction of only one side wall of the sterilizing container tub, in the direction of which fluid can be drained off. This can be achieved, for example, by a symmetrical configuration of the bottom.

All in all, it is advantageous for the sterilizing container tub to define a tub center plane which is aligned perpendicularly to the set-down plane and in relation to which the bottom is asymmetrically configured. For example, the fluid drainage surface can extend beyond a center of the bottom and thereby intersect this plane of asymmetry in order to conduct fluid to the fluid collection area arranged at a distance from the plane of asymmetry.

In particular, the fluid collection area is asymmetrical in relation to the plane of asymmetry.

Alternatively or additionally, it may be provided that the sterilizing container tub defines a tub center plane which is aligned perpendicularly to the set-down plane and in relation to which the bottom is symmetrically configured. This makes a constructional simplification of the sterilizing container tub possible. The plane of symmetry of the bottom can, in particular, be aligned perpendicularly to the aforementioned plane of asymmetry of the bottom.

It proves advantageous for the bottom to comprise or form depressions in the area of which the sterilizing container tub has set-down elements on the outside, which define the set-down plane. Owing to the formation of the depressions in the bottom, in particular, elevations can form on the outside of the sterilizing container tub, which define the set-down plane and can act as set-down elements via which the sterilizing container tub can contact a set-down surface. Separate set-down elements which are connected to the bottom from the outside can thereby be dispensed with. In this embodiment, it proves advantageous for the bottom to be formed by a bottom wall.

It is expedient for the depressions, which are adjacent to a section of the container wall in the direction of which the fluid drainage surface is inclined, to form part of the fluid collection area. This allows a constructional simplification of the sterilizing container tub. The depressions can hold fluid that is drained off from the fluid drainage surface in the direction of the container wall and thereby form part of the fluid collection area.

It may be provided that the aforementioned fluid channel of the fluid lifting device engages one of the depressions, so that collected fluid can enter the fluid channel.

It may be advantageously provided that the sterilizing container tub is of rectangular or substantially rectangular cross section with four side walls forming the container wall and depressions at corner areas of the sterilizing container tub, the fluid drainage surface being inclined in the direction of one of the side walls, and that at least one of the depressions adjacent to the side wall forms part of the fluid collection area. At least one, preferably two of the four depressions at the corner areas of the sterilizing container tub can form part of the fluid collection area which, for example, extends along the side wall in the direction of which the fluid drainage surface is inclined.

The bottom preferably has at the fluid collection area a bottom section which is aligned parallel to the set-down plane and is connected to the fluid drainage surface at a distance from the container wall. In this preferred embodiment, the fluid drainage surface does not extend directly as far as the container wall, but as far as a bottom section aligned parallel to the set-down plane. As a result, the inclined fluid drainage surface does not need to extend as far as the bottom wall. This makes it possible to achieve a low constructional height of the bottom.

The bottom section aligned parallel to the set-down plane can continue into one or more of the aforementioned depressions in the bottom, which forms/form part of the fluid collection area.

It proves expedient for the bottom section to extend from the fluid drainage surface as far as or substantially as far as the container wall. For example, the bottom section can be connected to the container wall on the side that faces away from the fluid drainage surface.

In a modification of the last-described advantageous embodiments of the sterilizing container tub in accordance with the invention, it may be provided that the fluid drainage surface extends directly as far as the container wall.

It is expedient for the bottom to comprise or form supporting elements for supporting a receptacle for surgical instruments and for the supporting elements to define a supporting plane aligned parallel to the set-down plane. A receptacle for instruments, in particular, a surgical screen basket can be positioned on the supporting elements. The supporting plane makes reliable positioning and, consequently, reliable supporting of the receptacle possible.

The distance of the supporting plane from the set-down plane is preferably the same as or greater than that of the fluid drainage surface therefrom. In particular, this can be understood as meaning that the fluid drainage surface does not project beyond the supporting plane into a receiving space defined by the sterilizing container tub. On the one hand, this allows reliable positioning of the receptacle for surgical instruments on the supporting elements. On the other hand, fluid can be drained off underneath the receptacle.

In a constructionally simple configuration, it is expedient for the supporting elements to be of planar configuration. For example, the supporting elements can be sections of the bottom and, in particular, of a bottom wall of the sterilizing container tub, which extend parallel to the set-down plane.

It is expedient for the bottom to have two supporting elements extending along two side walls of the sterilizing container tub arranged at a distance from each other, and for the fluid drainage surface to be arranged between the supporting elements. As a result, the receptacle can be set-down on the outside on the preferably planar supporting elements. Fluid such as condensate can be drained off from the fluid drainage surface underneath the receptacle. The supporting elements are preferably bottom sections which extend along longitudinal sides of the container wall in a longitudinal direction of the sterilizing container tub, the fluid drainage surface being arranged in its transverse direction between the supporting elements. The fluid drainage surface is expediently inclined in the direction of a transverse side wall of the container wall.

The present invention further relates to a surgical sterilizing container, comprising a surgical sterilizing container tub and a sterilizing container lid adapted to be detachably fitted on the sterilizing container tub. The surgical sterilizing container is adapted for holding surgical instruments for sterilization. The sterilizing container tub comprises a bottom and a container wall projecting from the bottom, the sterilizing container tub defines a set-down plane, and the bottom comprises or forms a fluid collection area for collecting fluid. The bottom comprises a fluid drainage surface which is inclined relative to the set-down plane and is in fluid connection with the fluid collection area for draining fluid in the direction of the container wall.

The advantages mentioned above in conjunction with the sterilizing container tub in accordance with the invention can be achieved with the sterilizing container in accordance with the invention so that reference can be made in this connection to the explanations given hereinabove.

FIG. 1 shows in perspective representation a preferred embodiment, denoted in its entirety by reference numeral 10, of a sterilizing container in accordance with the invention. The sterilizing container 10 serves to hold surgical instruments during the sterilization process. The instruments, not shown in the drawings, are usually arranged in a receptacle, not shown in the drawings either, for example, in a surgical screen basket held in the sterilizing container 10.

The sterilizing container 10 comprises a preferred embodiment of a sterilizing container tub 12 in accordance with the invention of generally rectangular shape, which has a bottom 14 and an outer wall 16 protruding from the bottom 14. The bottom 14 is formed by a bottom wall 15. The outer wall 16 comprises four side walls, namely two longitudinal side walls 17 and 18, which are joined to each other at the ends by two transverse side walls 19 and 20, respectively. The outer wall 16 is a container wall of the sterilizing container 10. The longitudinal side walls 17 and 18 define a longitudinal direction of the sterilizing container 10. The transverse side walls 19 and 20 define its transverse direction.

The sterilizing container 10 comprises a sterilizing container lid 22, which can be fitted sealingly on the sterilizing container tub 12 in order to cover it and close a container interior 24 defined by sterilizing container 10. The sterilizing container lid 22 can be detachably connected to the sterilizing container tub 12 by closure elements known per se.

The sterilizing container tub 12 defines a set-down plane 26 of the sterilizing container 10, which is a contact plane in which the sterilizing container tub 12 contacts a set-down surface on which it is set down. Where a set-down surface is aligned horizontally, as is usually the case, the set-down plane 26 is aligned horizontally.

Position and orientation details such as, for example, "at the top", "at the bottom" or the like relate in this context to a position of use of the sterilizing container 10 on a horizontal set-down surface and hence on a horizontally aligned set-down plane 26 in an operating position of the sterilizing container 10.

The sterilizing container tub 12, especially the bottom 14, is overall of symmetrical configuration in relation to a plane of symmetry 28, which is aligned perpendicularly to the set-down plane 26 and is a center plane of the tub. The plane of symmetry 28 runs centrally between the longitudinal side walls 17 and 18, in FIG. 4 perpendicularly to the plane of drawing and along line 5-5.

Furthermore, the sterilizing container tub 12, especially the bottom 14, is of asymmetrical configuration in relation to a plane of asymmetry 30, which is aligned perpendicularly to the set-down plane 26 and perpendicularly to the plane of symmetry 28 and which is a center plane of the tub, which runs centrally between the transverse side walls 19 and 20.

In corner areas of the sterilizing container tub 12 where the longitudinal side walls 17, 18 and the transverse side walls 19, 20 meet one another there are depressions 32 in the bottom 14. The depressions 32, like the remaining bottom 14, are formed during the forming of the sterilizing container tub 12 by a forming process, for example, by deep drawing.

Due to formation of the depressions 32, the bottom 14 has set-down elements 34 on the outside, which define the set-down plane 24.

The sections of the bottom wall 15 in the area of depressions 32 located opposite each other in the longitudinal direction are connected to each other by bottom sections 36 which extend along the longitudinal side walls 17 and 18. The bottom sections 36 extend in the longitudinal direction over approximately 60% of the length and in the transverse direction over approximately 25% of the bottom 14. The bottom sections 36 are of planar configuration and form supporting elements 38 which define a supporting plane 40 aligned parallel to the set-down plane 26. No sections of the bottom wall 14 extend beyond the supporting plane 40. A receptacle for surgical instruments, in particular, a surgical screen basket, can be reliably placed in an upright position on the supporting elements 38.

In the transverse direction, the bottom sections in the area of the depressions 32 are connected to each other along the transverse side wall 19 by a bottom section 44. Along the transverse side wall 20, the bottom sections in the area of the depressions 32 are connected to each other by a bottom surface section 45.

The bottom sections 44 and 45 define a common plane which is aligned parallel to the set-down plane 26 and is at a shorter distance from it than from the supporting plane 40 (FIG. 5). The bottom section 44 extends in the longitudinal direction over an area of approximately one quarter of the length of the bottom 14, the bottom section 45 over approximately 10% of the length of the bottom 14. At a distance from the transverse side wall 19, the bottom surface section 44 is connected to a fluid drainage surface 46 of the bottom 14, the connection being effected in the transverse direction of the bottom 14.

The fluid drainage surface 46 extends in the longitudinal direction from the bottom section 44 to the bottom section 45 and in the transverse direction between the bottom sections 36. The fluid drainage surface 46 thereby covers the center of the bottom 14 through which the plane of symmetry 28 and the plane of asymmetry 30 run. The fluid drainage surface 46 is of planar configuration and, in a plan view of the sterilizing container tub 12, is approximately trapezoidal with a base facing the transverse side wall 20. On the side opposite the base, the fluid drainage surface 46 is connected to the bottom section 44. All in all, the fluid drainage surface 46 extends over approximately one third of the surface of the bottom 14. It thereby covers approximately 60% to approximately 70% of the bottom surface in the longitudinal direction and approximately 50% of the bottom surface in the transverse direction.

The fluid drainage surface 46, in particular, the plane defined by it, is inclined at an angle of inclination 48 relative to the set-down plane 26. The fluid drainage surface 46 does not intersect the set-down plane as it only extends as far as the bottom section 44 in the direction of the set-down plane. The angle of inclination 48 is, in this case, less than 2°, for example, approximately 1.5°. The fluid drainage surface 46 is inclined in the direction of the transverse side wall 19 so that at its end facing the transverse side wall 19 it is at a shorter distance from the set-down plane 26 than at its end opposite the transverse side wall 19. The latter end starts from the supporting plane 40, and the end of the fluid drainage surface 46 that faces the side wall 19 is arranged in the plane defined by the bottom section 44.

The inclination of the fluid drainage surface 46 has the consequence that fluid, in particular, condensate formed during the sterilization process, is drained off from the fluid drainage surface 46 in the direction of the transverse side wall 19. Since the bottom section 44 and the bottom wall 15 in the area of the depressions 32 at the transverse side wall 19 are at a shorter distance from the set-down plane 26 than the fluid drainage surface 46 (apart from its connection with the bottom section 44) fluid is conducted to the bottom section 44 and the depressions 32 at the transverse side wall 19. The bottom 14 in the area of the bottom section 44 and of the depressions 32 at the transverse side wall 19 thereby forms a fluid collection area 50. Fluid drained off from the fluid drainage surface 46 collects in the fluid collection area 50, with fluid first being drained off into the depressions 32 at the transverse side wall 19. As the fluid level rises, fluid can also collect on the bottom section 44 which lies somewhat higher in relation to the bottom wall 15 in the area of the depressions 32.

In the configuration mentioned above, the fluid collection area 50 extends along the transverse side wall 19 which delimits a section of the fluid collection area 50 at the transition to the bottom wall 15. The fluid collection area 50 is, therefore, adjacent to the transverse side wall 19. Fluid can also be conducted from the bottom sections 36 in the longitudinal direction via slants of the bottom wall 15 into the depressions 32 at the transverse side wall 19.

The bottom 14 has a further fluid collection area 52 along the transverse side wall 20. The fluid collection area 52 is formed by the depressions 32 at the transverse side wall 20 and by the area lying between these in the transverse direction and delimited at the bottom by the bottom section 45. Fluid can also be drained off from the bottom sections 36 into the depression 32 at the transverse side wall 20. However, the total amount of fluid collecting in the fluid collection area 52 is substantially less than the amount of fluid collecting in the fluid collection area 50. This is due to the asymmetrical configuration of the bottom 14 relative to the plane of asymmetry 30 and the inclined fluid drainage surface 46 by which the predominant amount of fluid is drained off in the direction of the transverse side wall 19 into the fluid collection area 50.

Three through-openings are provided in the outer wall 16 to enable an exchange of media such as gas and/or fluid from the container interior 24 to the environment and conversely also when the sterilizing container 10 is closed. In contrast, the cover wall of the sterilizing container lid 22 and the bottom 14 are free of openings.

A first through-opening, not shown in the drawings, is formed in the transverse side wall 20. The through-opening is covered (FIG. 7) by a filter 54. The filter 54 is held by a filter retaining element 56 in the form of a retaining plate on the transverse side wall 20, thereby covering the through-opening. An exchange of media takes place between the environment and the container interior 24 through the filter 54 provided a first maximum pressure difference between the environment and the container interior is not exceeded or a second maximum pressure difference between the container interior 24 and the environment is not exceeded.

To enable an exchange of media in the latter cases and to avoid damage to the filter 54, the sterilizing container 10 comprises a valve device 58. The valve device 58 serves to open and close two through-openings 60 and 62 which are formed laterally next to each other in the transverse side wall 19 and at a distance from the bottom 14. In this case, the through-openings 60 are circular. The valve device 58 comprises an inlet valve 64 and an outlet valve 66, respectively, for closing and opening the through-openings 60 and 62.

Figure 3:
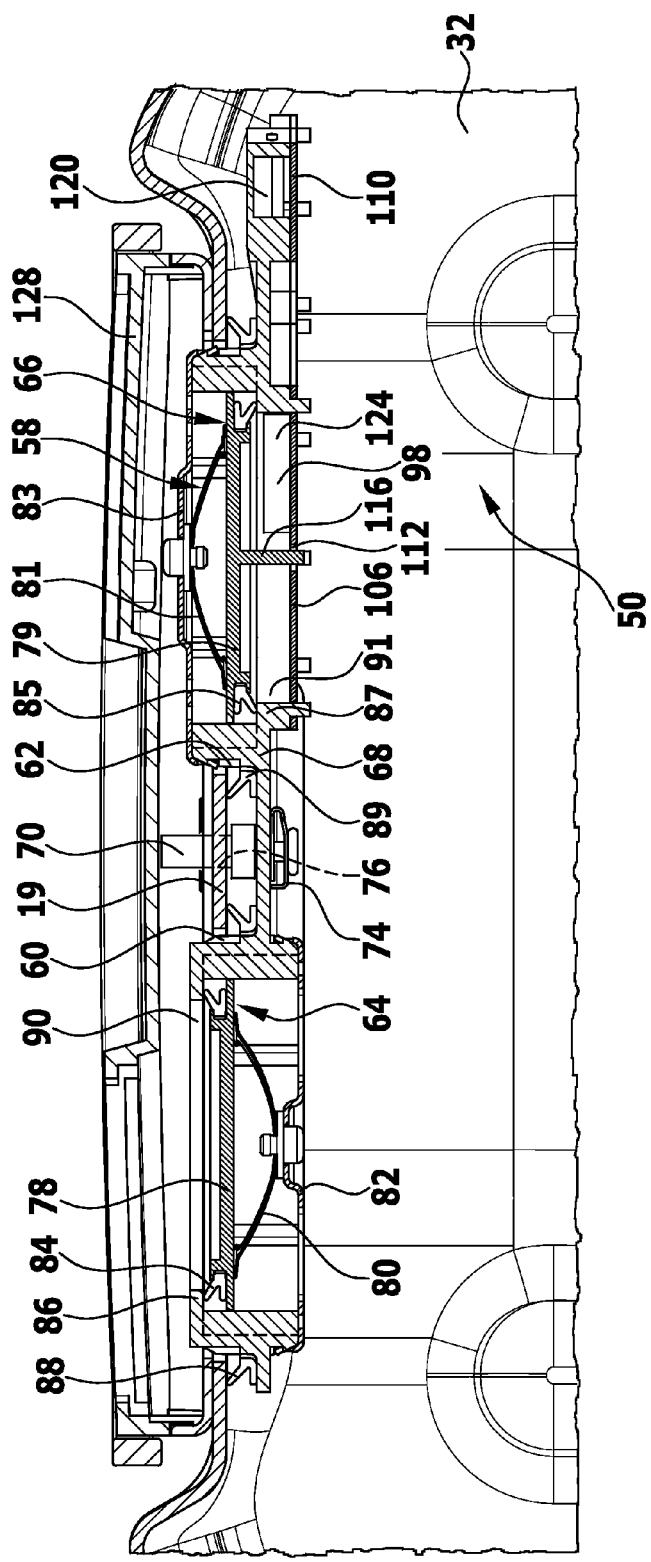
FIG. 3 a sectional view along line 3-3 in FIG. 1.

Associated with the valves 64 and 66 is a valve holder 68, in this case, of one-piece construction, on which the valves 64 and 66 are held. The valve holder 68 is of substantially plate-shaped configuration and is detachably connected to the transverse side wall 19. Connecting elements in the form of rivets (one rivet 70 is shown in FIG. 3) are provided for this purpose. The rivet 70 passes through a through-hole 72 in the valve holder 68 relative to which it is fixed in a force-locked and positively locked manner by a clamping element 74. The clamping element 74 is configured as a clamping rail by means of which both rivets can be fixed to the valve holder 68. With its free end, the rivet 70 passes through a through-hole 76 in the transverse side wall 19. The rivet 70 is in force-locked and positively locked engagement with the rim of the through-hole 76 so that it is thereby fixed to the transverse side wall 19.

To release the valve holder 68 from the transverse side wall 19, the force-locked engagement of the rivet with the clamping element 74 can be deactivated and the valve holder 68 with the valves 64 and 66 released from the sterilizing container tub 12. Conversely, the valve holder 68 can be connected to the sterilizing container tub 12 and fixed to it with the clamping element 74.

The inlet valve 64 and the outlet valve 66 are pressure-actuated valves with disk-shaped valve bodies 78 and 79, respectively, which are supported by elastic reset elements 80 and 81, respectively, in the form of yoke springs on media-permeable valve covers 82 and 83, respectively, which are connected to the valve holder 68. By means of sealing elements 84 and 85, respectively, in this case, in the form of lip seals, the valve bodies 78 and 79, respectively, can lie sealingly against valve seats 86 and 87, respectively, of the inlet valve 64 and the outlet valve 66, respectively. The valve seats 86 and 87 are formed by the valve holder 68. Via sealing elements 88 and 89, respectively, in this case, also in the form of lip seals, which extend around the rims of the through-openings 60 and 62, the valve holder is inserted sealingly into the through-openings 60 and 62. The valve holder 68 thereby reduces the cross-sectional area of the through-openings 60 and 62. When mention is made herein of opening and closing the through-openings 60 and 62 by the inlet valve 62 and the outlet valve 66, respectively, this refers to through-openings 90 and 91, respectively, in the valve holder 68, the rims of which are inserted into the through-openings 60 and 62 so that the cross sections of the through-openings 90 and 91 are smaller than those of the through-openings 60 and 62, respectively.

The sterilizing container 10 in accordance with the invention comprises a fluid lifting device 92 for lifting fluid out of the fluid collection area 50 and conducting it to the outlet valve 66. Fluid, in particular, condensate formed during the sterilization process, can be collected in the fluid collection area 50, in particular, in the depression 32 in the area of the transverse side wall 19 and the longitudinal side wall 17. The fluid lifting device 92 establishes a fluid connection between the fluid collection area 50 and the outlet valve 66 in order to remove fluid from the container interior 24.

For this purpose, the fluid lifting device 92 comprises a fluid channel 94 with a channel inlet opening 96 and a channel outlet opening 98. The fluid channel 94 comprises a first channel section 100 forming the channel inlet opening 96 and a second channel section 102 forming the channel outlet opening 98.

The first channel section 100 engages into the depression 32 in the corner area of the transverse side wall 19 with the longitudinal side wall 17 and, therefore, into the fluid collection area 50, but it does not contact the bottom wall 15.

Figure 2:
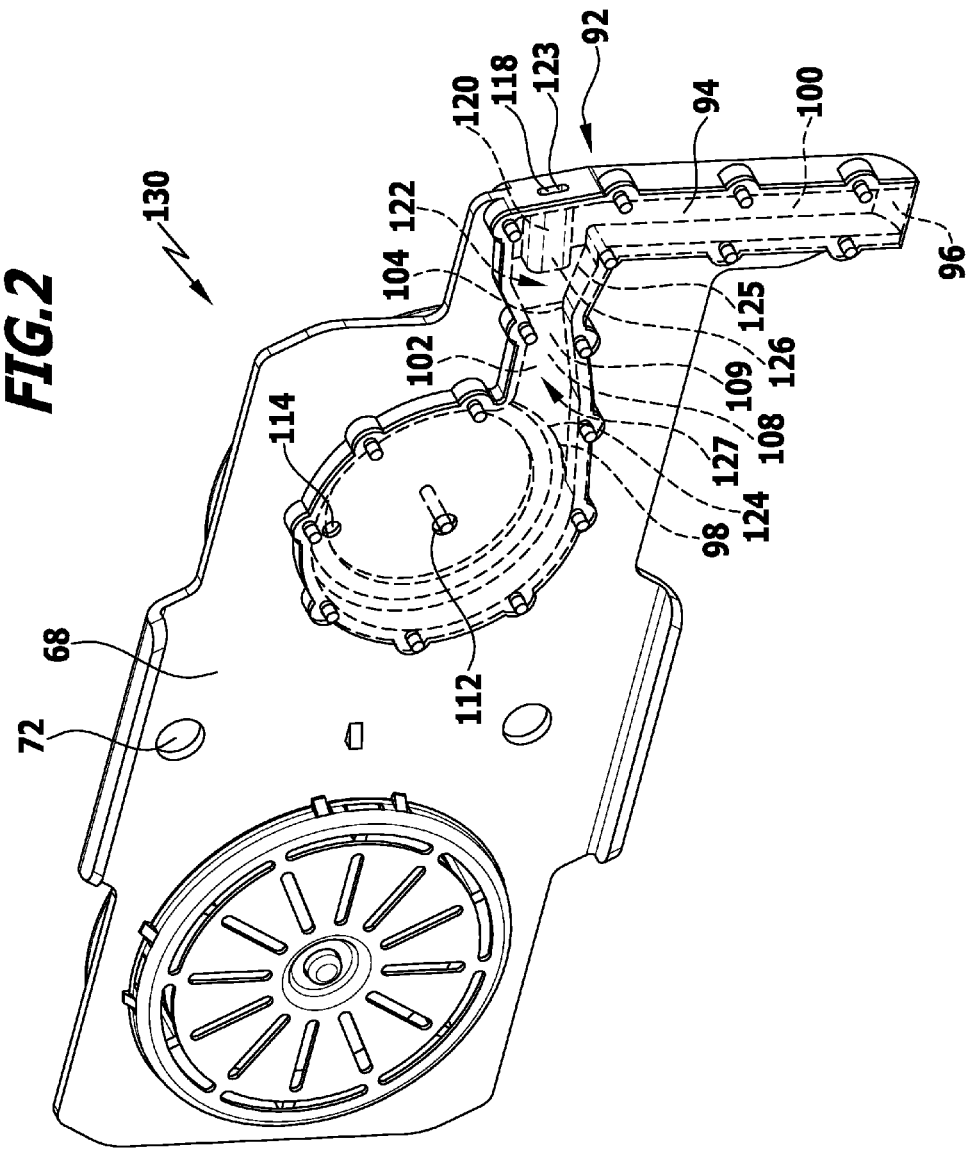
FIG. 2 a perspective representation of the fluid extraction device of the sterilizing container from FIG. 1.

The distance of the channel section 100 from the bottom wall is, for example, approximately 1 to 5 mm. The first channel section 100 is perpendicularly aligned relative to the set-down plane 26 and extends from it pointing upwards to approximately half of the height of the transverse side wall 19. The channel inlet opening 96 is directed at the bottom wall 15, which can be understood as meaning that the direction opposite to the direction of passage of fluid through the channel inlet opening 96 faces the bottom wall 15 (FIG. 1). The inlet opening 96 has an inclination in relation to the bottom wall 15 owing to a slant of the first channel section 100 at the end facing the bottom wall 15 (FIG. 2).

The second channel section 102 and the first channel section 101 are aligned at an angle relative to each other, which, in this case, is less than 90°. A direction defined by the second channel section 102 is inclined relative to the set-down plane 26, so that the second channel section 102 slopes down in the direction of the set-down plane 26. The channel outlet opening 98 is arranged at a side of the outlet valve 66 facing the bottom 14. The channel outlet opening 98 is directed at the upward flow side of the outlet valve 66, the direction of passage of fluid through the channel outlet opening 98 being substantially parallel to a plane defined by the disk-shaped valve body 79.

The second channel section 102 has a channel constriction 104 in the region of which the cross-sectional area of the fluid channel 94 is reduced in size. Downstream in the direction of flow of the fluid through the fluid channel 94, the cross section of the fluid channel 94 widens again after the channel constriction 104 up to the channel outlet opening 98.

The fluid channel 94 is formed by channel walls, which are formed by the valve holder 68 and a cover 106 connected thereto. For this purpose, there is formed in the valve holder 68 a groove 108 which forms a first channel wall 109 of the fluid channel 94. The channel wall 110 located opposite the channel wall 109 is formed by the cover 106. The channel walls 108 and 109 are formed by lateral groove walls of the groove 108 of the valve holder 68.

The cover 106 covers the groove 108 and the through-opening 91 in the valve holder 68 and, therefore, the outlet valve 66 on the inner side of the container. Owing to the aforementioned configuration, the fluid channel 94 extends between the valve holder 68 and the cover 106 which, in this case, is plate-shaped, substantially in a or parallel to a plane defined by the valve holder 68.

Owing to the rigid configuration of the valve holder 68 and the cover 106, the fluid channel 94 is dimensionally stable. The fluid channel 94 is detachably connected to the transverse side wall 19 via the valve holder 68.

In its section covering the through-opening 91, the cover 106 has two through-holes 112 and 114. A projection 116, in this case pin-shaped, on the valve body 79 engages in the central through-hole 112 when the outlet valve 66 is closed. The projection 116 and the through-hole 112 therefore serve as interacting aligning elements for aligning the valve body 79 relative to the cover 106. The through-hole 114 is arranged above the through-hole 112 and is located opposite the outer rim of the valve body 79 on the inner side of the container.

In the area of transition from the first channel section 100 to the second channel section 102, the fluid channel 94 has an inlet opening 118, in an extension of the direction defined by the second channel section 102. A sleeve-shaped insert 120, the passage of which is in alignment with the inlet opening 118, is arranged in the fluid channel 94, in the area in which the second channel section 102 branches off from the first channel section 100. The insert 120 and, consequently, the inlet opening 118 of the channel constriction 104 are located upstream in relation to the direction of flow of fluid through the fluid channel 94.

The fluid lifting device 92 comprises an injector 122 integrated in the fluid channel 94 and having an injector inlet opening 123, an injector outlet opening 124 and a suction opening 125. The injector inlet opening 123 is formed by the inlet opening 118 of the fluid channel 94, and the injector outlet opening 124 is formed by the channel outlet opening 98. The suction opening 125 is formed by the fluid channel 94 in its area surrounding the insert 120. The insert 120 has the function of a nozzle 126 of the injector 122. The injector further comprises a diffuser 127 which is integrated in the channel and a section of which is formed by the second channel section 102. The diffuser 127 extends from the channel constriction 104 to the channel outlet opening 98.

The purpose and function of the fluid lifting device 92 in combination with the outlet valve 66 are discussed in detail hereinbelow. The fluid lifting device 92 is provided in order to remove liquid, in particular, condensate, from the container interior 24 at the end of the sterilization process. The ambient pressure around the sterilizing container 10 is reduced until it is significantly below the internal pressure of the sterilizing container 10. Owing to the pressure difference, the pressure-controlled outlet valve 66 opens so that a pressure compensation with the ambient pressure can take place. Gas and fluid can exit from the sterilizing container 10.

To open the outlet valve 66, it proves to be advantageous that flow connections between the outlet valve 66 and the container interior 24 are formed by the through-holes 112 and 114 of the cover 106 and by the inlet opening 118 in the fluid channel 94, thereby bypassing the first channel section 100 when there is a sufficiently high level of condensate in the depression 32. Owing to the elevated internal pressure of the container, bypass flow paths circumventing the first channel section 100 can form through the inlet opening 118 and the second channel section 102 and also through the through-holes 112 and 114 when the outlet valve 66 is opened.

Depending on the height of the level of condensate in the fluid collection area 50, it is, however, also possible that a flow of gas will form through the first channel section 100 if the condensate level is so low that the first channel section 100 with the channel inlet opening 96 is not fully immersed in fluid.

When the outlet valve 66 opens, a suction flow is generated through the injector 122 by gas flowing through the inlet opening 118 and the nozzle 126 and through the second channel section 102 to the outlet valve 66. Owing to the channel constriction 104, a reduction in pressure occurs at the suction opening 125, and so a pressure difference forms in the fluid channel 94 between the suction opening 125 and the pressure at the channel inlet opening 96. This results in fluid being drawn out of the fluid collection area into the fluid channel 94. Fluid is then lifted further through the fluid channel 94 and conducted to the outlet valve 66, under constant suction flow through the injector 122.

Here it proves to be advantageous that the second channel section 102 is inclined in the direction of the set-down plane 26. This results in the flow of lifted fluid calming down and so after leaving the fluid channel 94 it does not exit from the sterilizing container 10 in a burst of spray. For this purpose, the diffuser 127 is also provided between the channel constriction 104 and the channel outlet opening 98 to ensure an increase in pressure and, at the same time, a calming of the flow of the fluid. Also, for protection against spraying of exiting fluid, a substantially plate-shaped cover element 128 is held on the outer side of the transverse side wall 19. The cover element 128 also serves to accommodate and mount a container handle of the sterilizing container 10.

The lifting of fluid out of the fluid collection area 50 through the fluid channel 94 under the action of the suction flow through the injector 122 is also possible and effective when the fluid level has dropped so far that the first channel section 100 is not completely immersed with the channel inlet opening 96 in the fluid. Even with a mixed flow of condensate and gas through the first channel section 100, it is found that under the action of the suction flow through the injector 122, fluid can continue to be lifted effectively out of the fluid collection area 50 and conducted to the outlet valve 66.

Furthermore, it proves to be advantageous, in particular, with a high level of condensate rising above the channel inlet opening 96, that bypass flow paths circumventing the first channel section 100 are present through the through-hole 112 and 114 and the inlet opening 118. This results in a pressure drop in the container interior 24 over more than only one flow path, and so fluid is not drawn off through the fluid channel 94 and removed from the sterilizing container 10 in a gush. Also the mechanical load on the sterilizing container 10 can be thereby reduced.

After closing the outlet valve 66, fluid that may still be present in the sterilizing container 10 can evaporate during the drying phase following the actual sterilization process due to the residual heat especially of the sterilizing container tub 12 and exit from the container interior 24 through the filter 54. In this connection, it proves to be advantageous that the fluid collection area 50 extends along the transverse side wall 19 so that the residual heat stored in the transverse side wall 19 is also effective for evaporating fluid. The same applies to the fluid collection area 52 which extends along the transverse side wall 20.

The provision of the fluid lifting device 92 proves to be advantageous for effectively lifting a large amount of fluid and removing it from the container interior 24 even before the actual drying phase of the sterilization process starts. The drying phase can thereby be considerably shortened.

The provision of the drainage surface 46 and of the fluid collection area allows a large amount of the fluid that forms, in particular, condensate, to be collected at the transverse side wall 19 so that it can be lifted at it by the fluid lifting device 92 and conducted to the outlet valve 66.

Furthermore, it is particularly expedient that the bottom 14 is free of any through-openings. Valves for closing the bottom 14 can thereby be dispensed with, and the bottom 14 forms a sterile barrier. The risk of germs entering by way of through-openings in the bottom, as is the case with sterilizing containers having fluid draining valves in the bottom, can thereby be avoided also after completion of the sterilization process. Damage to or malfunction of a fluid draining valve can also be prevented.

The outlet valve 66 and the fluid lifting device 92 are, in this case, part of a preferred embodiment of a surgical fluid extraction device, shown perspectively in FIG. 2 and denoted by reference numeral 130, which is used in the sterilizing container 10. The fluid extraction device 130 further comprises the valve holder 68 and the inlet valve 64. It may alternatively be provided that the inlet valve 64 is not held in the valve holder 68 and, consequently, is not part of the fluid extraction device 130. As mentioned, the fluid extraction device 130 can be detachably connected to the transverse side wall 19 which, in addition to facilitating assembly, also enables it to be exchanged when required.

What is claimed is:

1. Surgical sterilizing container tub on which a sterilizing container lid is adapted to be detachably fitted for formation of a surgical sterilizing container for holding surgical instruments for sterilization, the sterilizing container tub comprising:
a bottom and a container wall projecting from the bottom, the sterilizing container tub defining a set-down plane, and
the bottom comprising or forming a fluid collection area for collecting fluid,
wherein:
the bottom further comprises or forms:
a fluid drainage surface which is inclined relative to the set-down plane and is in
fluid connection with the fluid collection area for draining fluid in a direction of
the container wall, and
depressions which are adjacent to a section of the container wall in the direction
of which the drainage surface is inclined and which form part of the fluid
collection area,
the bottom is free of through-openings,
the size of the fluid drainage surface comprises at least 30% of the bottom surface, and
in the area of the depressions, set-down elements are provided on an outside of the bottom, which set-down elements define the set-down plane.

2. Sterilizing container tub in accordance with claim 1, wherein an inclination of the fluid drainage surface relative to the set-down plane is one of less than 10°, less than 5°, or less than 2°.

3. Sterilizing container tub in accordance with claim 1, wherein the fluid collection area is further formed by a further depression in the bottom.

4. Sterilizing container tub in accordance with claim 1, wherein:
a bottom wall forms the bottom, and the bottom wall forms at least one of the fluid drainage surface and the fluid collection area.

5. Sterilizing container tub in accordance with claim 1, wherein the fluid collection area is arranged off-center on the bottom.

6. Sterilizing container tub in accordance with claim 1, wherein the fluid collection area extends along a section of the container wall.

7. Sterilizing container tub in accordance with claim 1, wherein:
the sterilizing container tub is of rectangular or substantially rectangular cross section with four side walls forming the container wall, and
the fluid drainage surface is inclined in the direction of one of the side walls for draining fluid in the direction of the side wall.

8. Sterilizing container tub in accordance with claim 7, wherein the fluid collection area is adjacent to the side wall in the direction of which the fluid drainage surface is inclined for draining off fluid.

9. Sterilizing container tub in accordance with claim 1, wherein the fluid drainage surface extends beyond a center of the bottom.

10. Sterilizing container tub in accordance with claim 1, wherein the sterilizing container tub defines a tub center plane which is aligned perpendicularly to the set-down plane and in relation to which the bottom is asymmetrically configured.

11. Sterilizing container tub in accordance with claim 10, wherein the fluid drainage surface extends beyond a center of the bottom and intersects the tub center plane.

12. Sterilizing container tub in accordance with claim 1, wherein the sterilizing container tub defines a tub center plane which is aligned perpendicularly to the set-down plane and in relation to which the bottom is symmetrically configured.

13. Sterilizing container tub in accordance with claim 1, wherein:
the bottom further comprises or forms supporting elements for supporting a receptacle for surgical instruments, and
the supporting elements define a supporting plane extending parallel to the set-down plane.

14. Sterilizing container tub in accordance with claim 13, wherein:
the bottom further comprises or forms two of the supporting elements, each extending along one of two side walls of the sterilizing container tub,
the two supporting elements are arranged at a distance from each other, and
the fluid drainage surface is arranged between the two supporting elements.

15. Surgical sterilizing container, comprising:
a surgical sterilizing container tub, and
a sterilizing container lid adapted to be detachably fitted on the surgical sterilizing container tub,
the surgical sterilizing container being adapted for holding surgical instruments for sterilization,
the surgical sterilizing container tub comprising a bottom and a container wall projecting from the bottom,
the sterilizing container tub defining a set-down plane, and
the bottom comprising or forming a fluid collection area for collecting fluid,
wherein:
the bottom further comprises or forms:
a fluid drainage surface which is inclined relative to the set-down plane and is in fluid connection with the fluid collection area for draining fluid in a direction of the container wall, and
depressions which are adjacent to a section of the container wall in the direction of which the drainage surface is inclined and which form part of the fluid collection area,
the bottom is free of through-openings,
the size of the fluid drainage surface comprises at least 30% of the bottom surface, and
in the area of the depressions, set-down elements are provided on an outside of the bottom, which set-down elements define the set-down plane.

* * * * *